(12) United States Patent
Whalen et al.

(10) Patent No.: US 11,365,140 B2
(45) Date of Patent: Jun. 21, 2022

(54) DECISION SUPPORT SYSTEM AND METHOD FOR WATER TREATMENT

(71) Applicant: LUMINULTRA TECHNOLOGIES LTD., Fredericton (CA)

(72) Inventors: Patrick Andrew Whalen, Fredericton (CA); Jordan Jeremy Schmidt, Halifax (CA)

(73) Assignee: LUMINULTRA TECHNOLOGIES LTD., Fredericton (CA)

( * ) Notice: Subject to any disclaimer, the term of this patent is extended or adjusted under 35 U.S.C. 154(b) by 53 days.

(21) Appl. No.: 16/754,324

(22) PCT Filed: Oct. 29, 2018

(86) PCT No.: PCT/CA2018/051365
§ 371 (c)(1),
(2) Date: Apr. 7, 2020

(87) PCT Pub. No.: WO2019/084675
PCT Pub. Date: May 9, 2019

(65) Prior Publication Data
US 2020/0331783 A1 Oct. 22, 2020

Related U.S. Application Data

(60) Provisional application No. 62/579,263, filed on Oct. 31, 2017.

(51) Int. Cl.
*C02F 3/00* (2006.01)
*C02F 3/12* (2006.01)
(Continued)

(52) U.S. Cl.
CPC ............... *C02F 3/006* (2013.01); *C02F 3/12* (2013.01); *G01N 33/1806* (2013.01);
(Continued)

(58) Field of Classification Search
None
See application file for complete search history.

(56) References Cited

U.S. PATENT DOCUMENTS 4,385,113 A 5/1983 Frosch
6,005,964 A * 12/1999 Reid .................. G01N 15/1475
378/42
(Continued)

FOREIGN PATENT DOCUMENTS

CN 105948374 A 9/2016
EP 0708390 A2 4/1996
(Continued)

OTHER PUBLICATIONS

European Patent Application No. 18873615.1 Extended European Search Report dated Jun. 15, 2021.
(Continued)

*Primary Examiner* — Chester T Barry

(57) ABSTRACT

A decision support system and method can be used to control a water treatment or distribution system. The decision support system collects data from multiple water system operators and analyses the data for a selected water system according to one or more rules or algorithms. The system returns data, optionally including alerts or predictions, to the system operator. Optionally, the decision support system uses machine learning applied to (i) historical data from a selected water system and/or (ii) data from other water systems to modify the rules or algorithms used to analyze current data from a selected water system. In some embodiments, the data collected includes microbial population data such as ATP data, optionally including derivatives of microbial population data; microbial speciation information; or, metagenomic data.

20 Claims, 2 Drawing Sheets

(51) Int. Cl.
*G01N 33/18* (2006.01)
*C02F 103/10* (2006.01)

(52) U.S. Cl.
CPC .... *C02F 2103/10* (2013.01); *C02F 2209/008* (2013.01); *C02F 2209/36* (2013.01)

(56) References Cited

U.S. PATENT DOCUMENTS

| | | | |
|---|---|---|---|
| 6,093,322 | A | 7/2000 | Bongards |
| 6,408,227 | B1* | 6/2002 | Singhvi ................ C02F 1/008 700/266 |
| 6,599,712 | B1 | 7/2003 | Sakakibara et al. |
| 6,808,630 | B2 | 10/2004 | Yang |
| 8,357,299 | B2 | 1/2013 | Ginzburg et al. |
| 9,475,715 | B2 | 10/2016 | Elger et al. |
| 10,545,327 | B2* | 1/2020 | Barral ................ G02B 21/365 |
| 2001/0038450 | A1 | 11/2001 | McCaffrey et al. |
| 2008/0270328 | A1* | 10/2008 | Lafferty ................ E21B 43/00 706/12 |
| 2015/0159127 | A1* | 6/2015 | Guerini ................ C12M 23/58 435/70.3 |
| 2015/0322481 | A1 | 11/2015 | Davenport et al. |
| 2015/0337358 | A1 | 11/2015 | Driscoll et al. |
| 2016/0297697 | A1 | 10/2016 | Buschmann |

FOREIGN PATENT DOCUMENTS

| | | |
|---|---|---|
| EP | 1992946 A1 | 11/2008 |
| GB | 2514609 A | 12/2014 |
| JP | 4340239 B2 | 10/2009 |
| JP | 5049748 B2 | 10/2012 |
| WO | 9719353 A1 | 5/1997 |
| WO | 2005097968 A1 | 10/2005 |
| WO | 2006134698 A1 | 12/2006 |
| WO | 2016159154 A1 | 10/2016 |

OTHER PUBLICATIONS

International Patent Application No. PCT/CA2018/051365, International Preliminary Reporton Patentability dated May 14, 2020.
International Patent Application No. PCT/CA2018/051365, International Search Report and Written Opinion dated Jan. 28, 2019.

* cited by examiner

DECISION SUPPORT SYSTEM AND METHOD FOR WATER TREATMENT

RELATED APPLICATIONS

This application is a National Stage Entry of International Application No. PCT/CA2018/051365, filed Oct. 29, 2018, which claims the benefit of U.S. Application Ser. No. 62/579,263, filed Oct. 31, 2017, which is incorporated herein by reference.

FIELD

This specification relates to systems and methods for operating or controlling water treatment or distribution systems including, for example, wastewater treatment plants.

BACKGROUND

The control of water treatment and distribution systems can involve measuring operational data and adjusting control parameters so as to keep the measured data within desired ranges. Several methods have been developed to provide automatic or algorithmic control over some aspects of water system operation. In U.S. Pat. No. 6,093,322, the nitrification and denitrification phases in a wastewater treatment plant are controlled considering measurements of redox potential. Manipulations of the redox data produce input switch signals that are connected via a logic circuit to issue an output signal for ending a denitrification cycle. In U.S. Pat. No. 8,357,299, an on-line process control system considers resistance values to adjust operational parameters of an immersed membrane system. The operational parameters may have discrete states and are adjusted according to a hierarchy. In U.S. Pat. No. 6,408,227 a system predicts operational parameters for a water treatment plant using predictive equations based on historical operations data. In U.S. Pat. No. 6,808,630, present values of measured attributes in a wastewater treatment plant are compared to optimum set points of dissolved oxygen and solids retention time using a neural network control program with a back propogation algorithm. U.S. Pat. No. 9,475,715 describes a wastewater treatment process with automatic control systems of nitrification and denitrification capacity, solids retention time, biological phosphorous removal and the removal of water from a containment device.

INTRODUCTION

This specification describes a decision support system for a water treatment or distribution system (collectively called water systems) and related methods. The decision support system collects input data from a water system and analyses the data according to one or more rules or algorithms. The input data preferably includes microbial population data as well as measurements of one or more physical, chemical or electrical parameters. Preferably, the decision support system uses data from multiple water systems to determine or modify aspects, such as numerical thresholds or ranges, that are part of the rules or algorithms applied a selected water system. The decision support system may produce an output that includes an assessment of the current operation of a water system or a prediction, recommendation or warning about the future operation of the water system. Optionally, the decision support system may provide automated process control of one or more aspects of a water system.

DETAILED DESCRIPTION OF ONE OR MORE EMBODIMENTS

Figure 1:
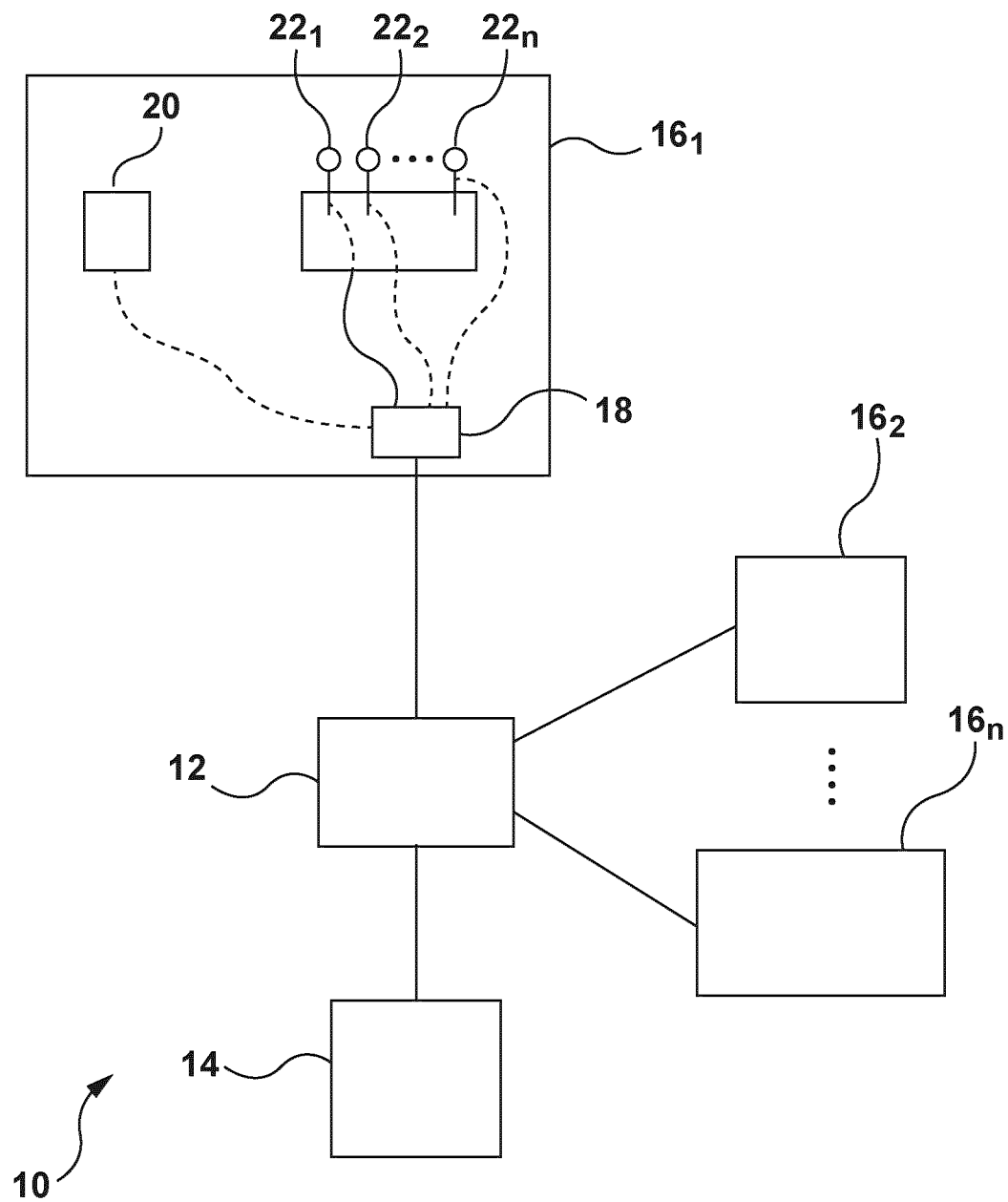
FIG. 1 shows a schematic drawing of a decision support system.

A decision support system collects input data from multiple analogous water systems and analyses the data for each water system according to one or more rules or algorithms. The decision support system outputs data, for example to a system operator, regarding operation of a selected water system, or directly controls an aspect of the water system. The output data optionally includes alerts, predictions, recommendations or inputs to controlled devices. The input data preferably includes data relating to one or more microbial populations, which may relate to all microorganisms or selected microorganisms. The decision support system preferably considers data from multiple water systems in producing an output for a selected water system. For example, the decision support system may use data from multiple water systems to determine or modify thresholds or ranges that are part of the rules or algorithms that will be applied to data from a target water system.

Optionally, the decision support system uses machine learning applied to (i) historical data from a selected water system and/or (ii) data from other analogous water systems, to modify the rules or algorithms used to analyze current data from a selected water system. Optionally, the decision support system may classify water systems, for example into industry and/or application subsets, and collect or convert data from water systems in a subset according to a common model. The analysis of data from one water system may consider data from multiple water systems in the same subset. Optionally, the decision support system can be initially implemented with pre-selected attributes, for example rules and membership functions, but evolve to operate considering a mixture of expert and machine learned solutions or entirely on machine learned solutions.

In some examples, a water system is modeled in the decision support system as having one or more data sources, each data source characterized by its location in a water system and the parameter measured. Preferably, at least one of the data sources includes microbial population data. Optionally, the data from one or more data sources may be converted into a one or more states (i.e. classes or ranges) which may be named, for example, as red-yellow-green or high-low. Membership in the states may be mutually exclusive or according to a membership function that allows simultaneous membership in multiple states (i.e. 0.6 green, 0.4 yellow). The dividing lines between the states can be initially determined or later varied based on one or more of a) arbitrary, user defined or default values, b) expert knowledge, c) experience, optionally including machine learning, based on past data from a selected plant or, d) experience, optionally including machine learning, from other analogous plants. In some examples, the decision support system implements an algorithm such as a decision tree or fuzzy logic considering the membership of data in one or more states to return an output. The algorithm may return, for example, an alert, recommendation, prediction or control signal.

Microbial population data can include data relating to the number (i.e. concentration) of microorganisms present in the water. Optionally, the data may relate to one or more of the numbers of live, dead and total (live and dead) microorganisms present in the water, or one or more ratios involving live, dead or total microbial counts or concentrations. Optionally, the data may relate to one or more of a) the number or concentration of all microorganisms present in the water and b) the number or concentration of one or more subsets of microorganism present in the water, for example a species, genera (i.e. class, order or phylum) or functional class (i.e. nitrifiers, denitrifiers, aerobes, anaerobes, facultative aerobes, facultative anaerobes, sulfur-reducing bacteria, iron-reducing bacteria, or corrosion inducing bacteria) of microorganisms. The microbial population data may be provided automatically, for example by an automated sampling device in communication with the decision support system, or the microbial population data may be provided by a user through an interface with the decision support system. The microbial population data may be generated on site or by sending samples to another location for analysis.

Exemplary types of microbial population data include AxP (i.e. ATP, ADP or AMP) measurements, cell culture data, flow cytometry, immunoassays, and metagenomic data such as PCR measurements (i.e. quantitative polymerase chain reaction (qPCR) or reverse transcription (RT) PCR), RNA quantification or sequencing data (i.e. nanopore sequencing data). Data considered by the decision support system may also include supplemental data, preferably including one or more water treatment process parameters that can be correlated to microbial growth.

FIG. 1 shows an example of a decision support system (DSS) 10. The DSS 10 has a server 12 or server system, which may include for example one or more cloud based servers or portions of servers. The server 12 is programed and monitored through a server interface computer 14. In particular, the server 12 is programed to run one or more analytical methods applied to data from water treatment systems $16_1$ to $16_n$. Within each water treatment system 16, a router 18 conveys data from sensors $22_1$ to $22_n$ to sever 12. In the example shown, data is collected and communicated automatically by automated online sensors 22. Alternatively, a human operator may be involved in collecting and/or communicating some or all of the data in place of a sensor 22. A system operator can interact with the server 12 through one or more user interface devices 20, for example a mobile computer such as a tablet, laptop, or smartphone, or a stationary computer such as a programmed logic controller or general-purpose computer.

The DSS 10 may be used with a set of analogous water treatment systems. Alternatively, the DSS 10 may be set up for use by diverse industries and applications. In this case, information regarding a particular system 16 may be entered through the user interface after indicating an industry and application (i.e. water treatment system and/or process type) used to classify the systems 16 into analogous subsets. For example, the user may select their industry and application from drop down menus populated with options supported by the DSS 10. The DSS 10 then creates subsets of systems 16 that have the same industry and application. To the extent that the DSS 10 considers data from other systems 16 when analyzing a selected systems 16, the data from other systems may be limited to systems from the same industry and application, or optionally include data from related industries and applications through conversion rules or with weighting factors. Examples of possible industries include, for example, chemical products; cooling water; drinking water; health care and life sciences; metalworking; process water; upstream oil and gas industries; wastewater treatment; ballast water; biogas generation; petroleum and fuels; aquaculture; agriculture and, surface hygiene. Examples of possible applications within an industry include, for example, within the industry of wastewater treatment: activated sludge; membrane bioreactor; trickling filter; and, anaerobic digester applications. For further example, applications within the drinking water industry could include: conventional treatment; membrane filtration; and, municipal distribution, among others.

A system operator (which may include an agent, contractor or employee of an operator) also uses interface device 20 to build a model of the system 16 in the DSS 10. For example, the DSS 10 may provide tools through the user interface device 20 that allow an operator to select or create a process flow diagram supported by the DSS 10. The system operator also enters information on the type of sensors 22 that will send data to the server 12, the location of the sensors 22 in the process flow diagram, and optionally an identifier for each sensor 22.

The DSS 10 can consider combinations or derivations of data from a sensor 22. In some cases, information from physical sensors or other test equipment may be manipulated such that a sensor in the model indicates a location and/or what is measured at that location that differs from the physical device used to take the measurement and what exactly is measured. For example, raw data may be converted, for example by the calculation of ratios, rates, concentrations or other derived values, before data from a sensor is communicated to the server 12, or by the program running on server 12.

The process flow diagram may optionally be more or less complicated than the actual systems 16, in some cases with appropriate conversions or corrections. For example, two parallel aeration tanks may be modeled as one aeration tank of the same combined volume. In another example, an anoxic tank and an aerobic tank forming a nitrification—denitrification loop may be modeled as a single bioreactor. In other examples, the model may have a process unit that does not exist in the actual system, with the extra model process unit defined as having no sensors and optionally with no effect, for example no hydraulic retention time (HRT). The DSS 10 may also provide a sample process flow diagram with a set of available sensors and locations that can be selected from. In some cases, a sensor location in the process flow diagram can be selected that is not exactly the same as the sensor location in the real system 20. For example, a sensor in an outlet pipe in a real system 16 can, in at least some cases, be modeled as a sensor in a fully mixed tank connected to the outlet pipe in the process flow diagram model of the system 16.

For some industries and/or applications, the DSS 10 may also collect additional information that may be used to restrict analysis to a portion of a subset of systems 16, or select additional rules to be used when considering data from some systems. Additional information can include the source of water to the plant, for example high purity water, municipal water, groundwater, surface water, seawater, municipal wastewater, food and beverage wastewater, pulp & paper wastewater or petrochemical industry water (i.e. produced water or frac water). In other examples, additional information may include type of biocide used. In other examples, additional information may include non-water sensors such as sensors connected to a powder, or organic fluid in a process.

Figure 2:
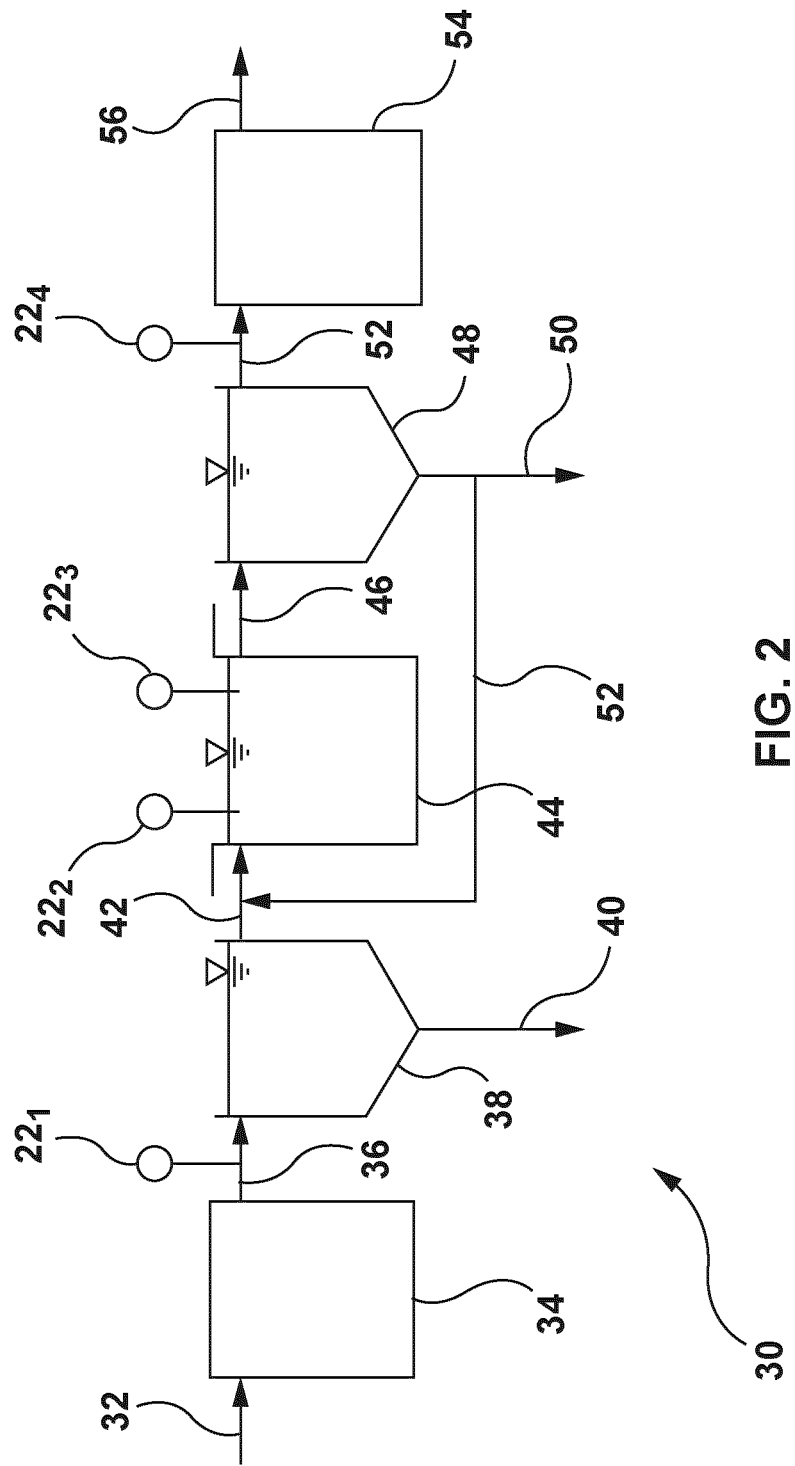
FIG. 2 shows an example of a process flow diagram for an activated sludge wastewater treatment plant.

FIG. 2 gives an example of a model of treatment plant for the selections: industry—wastewater treatment; application—activated sludge. The model is based on a model plant 30 which is an activated sludge plant. Raw sewage 32 enters headworks 34 which in an actual plant could involve, for example, flow buffering, coarse screening or other pretreatment steps. Pre-treated influent 36 flows to a primary treatment unit 38, which in an actual plant might be, for example, a micro-sieve or clarifier. Primary treatment unit 38 produces primary sludge 40 and primary effluent 42. Primary effluent 42 is treated in a bioreactor 44 which in an actual plant may include, for example, one or more aerobic process tanks and optionally one or more anoxic or anaerobic tanks. Secondary effluent 46 flows from the bioreactor 44 to a secondary separator 48 which in an actual plant might be for example a membrane filtration unit or a clarifier. Secondary separator 48 produces waste activated sludge 50, return activated sludge 52 and secondary effluent 52. The secondary effluent 52 flows to an optional polishing unit 54 to produce the final effluent 56. In an actual plant, the polishing unit 54 may be, for example, a disinfection unit or a tertiary filter. The model plant 30 has a first ATP sensor 22(1) in the pre-treated influent 36, a second ATP sensor 22(2) in the bioreactor 44, a mixed liquor suspended solids (MLSS) sensor 22(3) in the bioreactor, and a BOD sensor 22(4) in the secondary effluent 52. The actual plant has the same or similar sensors in the same or similar locations. The sensors are preferably automated sensors that collect and report data to the server 12 of FIG. 1 according to a regular schedule.

The ATP sensor lyses cells in a sample, adds a bioluminescent agent reactive with ATP (i.e. luciferase) to the sample, and then senses the strength of radiation emitted from the sample in a luminometer. Each ATP sensor may return three values—dissolved ATP, cellular ATP (cATP) and total ATP. The dissolved ATP represents the number of dead microorganisms in the water. Cellular ATP represents the number of living microorganisms. The total ATP represents the number of living and dead microorganisms in the water.

The ATP sensors 22 in the example shown are automated on-line sensors that produce results from a sidestream flow of water. For example, the EZ-TAP on-line ATP analyzer is available from Applitek and another automated on-line ATP detector is commercially available from Biotrace. The ATP sensors 22 may report results automatically to DSS 10 through a telecommunications or internet connection. Alternatively, the ATP sensor 22 may be a manual or semi-automated ATP test kit, or a plate count analysis, with results transferred to the DSS 10 by a user through an interface device 20. Optionally, ATP data can be replaced with other AxP (i.e. ADP or AMP) data.

Optionally, an ATP sensor may be replaced by another device that provides population data such as a metagenomic testing device. A metagenomic device produces a measure of microbial population by quantifying the amount of DNA in a sample. The measurement typically indicates total (alive and dead) microorganisms but sample preparation techniques (for example centrifugation) may be used to reduce the amount of dead cells measured. Alternatively, propidium monoazide (PMA) may be used to inhibit amplification of dead cell DNA in methods involving amplification. The metagenomic testing device may be located on site or in an off-site laboratory. An example of an on-site device is the HUNTER system from Instant Labs, which uses qPCR to quantify nucleic acid extracted from a grab sample to produce measurements on site. RT-PCR may also be used. Alternatively, a sequencing device, for example a nanopore sequencing device such as the MINION system from Oxford Nanopore, can be used to provide an on-site count of all microorganisms in a sample.

Optionally, a sequencing device can be used (alternatively or additionally) to provide data on the population of a subset of the microorganisms. Off-site processing of samples is available, for example from Microbe Detectives, to break down the total population in a sample by microbial type or species. Other off-site services are available to determine the population of specific types of microorganisms, for example sulfur-reducing bacteria (SBR) from Instant Labs. In some cases, on-site kits are available to quantify the microorganisms of a selected type. For example, IELAB provides kits using PCR based analysis to quantify *Legionella* microorganisms. Data from general-purpose devices, such as MINION device, may also be analyzed to provide population data on a selected set of microorganisms. Population data relating to a selected type or species of bacteria can also be obtained by other methods such as cell cultures, fluoromoetry or flow cytometry. A user can transfer the data from an onsite metagenomic or other testing device, or an offsite laboratory, to the DSS 10 through an interface device 20 if direct communication from an onsite testing device is not available.

In some examples, data from the sensors 22 can be allocated into ranges or states such as High-Low or Red-Yellow-Green. Once allocated into ranges, the data can be used to indicate the operational state of the system. In Table 1, for example, the data is interpreted through a decision tree. In the decision tree, each type of data is considered at a node to determine which branch to follow to the next node, ending at a unique branch of the decision tree represented by a cell in the right hand column of Table 1.

TABLE 1

| cATP Bioreactor | MLSS Bioreactor | BOD Effluent |
|---|---|---|
| High | High | High |
|  |  | Low |
|  | Low | High |
|  |  | Low |
| Low | High | High |
|  |  | Low |
|  | Low | High |
|  |  | Low |

The right hand column of FIG. 1 contains one cell for every possible permutation and combination of sensor and sensor data range/state. Some or all of these cells may be linked to outputs such as predictions, alerts or control signals. For example, the cell reached through the path of cATP Bioreactor=High; MLSS Biorector=High; and BOD Effluent=Low can be linked to an Alert sent to the system operator indicating that there is an opportunity for MLSS optimization to decrease aeration cost. In another example, the cell reached through the path of cATP Bioreactor=Low; MLSS Biorector=Low; and BOD Effluent=Low can be linked to an Alert sent to the system operator indicating that not enough sludge is being recycled and that less sludge should be wasted to allow the biomass to recover.

The High range for BOD Effluent may contain at least some effluent BOD concentrations that are unacceptably high (i.e. 25 mg/L or more) and indicate a failure of a subject water system. The Decision Support System might or might not alert a system operator to the failure, since the operator is likely to be independently aware of the failure. However, depending on the cATP and MLSS values, the DSS 10 may provide an Alert suggesting a change in operation. In the event that the DSS 10 does not provide any Alert, or a recommendation accompanying the Alert does not correct the failure, the relevant cATP/MLSS/BOD Effluent is flagged in the DSS 10 as an error. The DSS 10 then considers one or more other analogous water systems and attempts to correct the error. The DSS 10 may consider the most similar (i.e. in size, location or other factors) analogous water system, the best performing analogous water system, or may consider a subset of similar water systems having the same industry and application. The subset may contain all water systems in the same industry and application or a further subset selected, for example, based on similarity of size and/or location.

In one example, the DSS 10 determines the optimal, or optimal range, of cATP and MLSS values by taking the mean and 95% confidence interval of cATP and MLSS the subset. Optionally, a weighted average within the subset may be used, with better performing (i.e. typically lower BLD effluent) water systems weighted more heavily. The decision tree for the failed system is then adjusted to recommend operation within the 95% confidence interval. In addition, the failed water system operator may be provided with a workplan with instructions for how to adjust the water system to have cATP and MLSS within the optimal ranges.

In another example, the subset is polled to see if the decision tree for another one or more water systems would produce a different Alert or recommendation from the same cATP, MLSS and BOD date. If so, then the alternative Alert and recommendation from the other systems is proposed to the water system operator. If successful, the alternative rule is flagged as being successful, and replaces the failed rule in the decision tree for the subject water system. In a similar option, the structure of the decision tree for the subject water system may be kept unchanged, but one or more thresholds or ranges of cATP, MLSS and BOD are modified such the decision tree will produce the successful Alert and recommendation.

In another example, the subset is polled to see if another water system with similar cATP and MLSS values nevertheless has lower BOD effluent than the subject water system. In this case, any other values known for the other water system are compared to the subject water system to determine if a more complex decision tree is required.

The data from sensors 22 may optionally be manipulated before it is considered. For example, Biomass Stress Index (BSI) is a parameter (ratio) obtained by dividing dissolved ATP (representing the number of dead microorganisms) by total ATP (representing the cumulative number of live or dead microorganisms). Active Biomass Ratio (ABR) is a parameter obtained by dividing active biomass suspended solids (ABSS—the number of living microorganisms) by MLSS or TSS. Table 2 gives an example of a decision tree based analysis for the activated sludge model of FIG. 2 using these parameters.

TABLE 2

| BSI Influent | BSI Bioreactor | ABR Bioreactor | MLSS Bioreactor |
|---|---|---|---|
| Red | Red | Red | High |
|  |  |  | Low |
|  |  | Green | High |
|  |  |  | Low |

TABLE 2-continued

| BSI Influent | BSI Bioreactor | ABR Bioreactor | MLSS Bioreactor |
|---|---|---|---|
|  | Green | Red | High |
|  |  |  | Low |
|  |  | Green | High |
|  |  |  | Low |
| Green | Red | Red | High |
|  |  |  | Low |
|  |  | Green | High |
|  |  |  | Low |
|  | Green | Red | High |
|  |  |  | Low |
|  |  | Green | High |
|  |  |  | Low |

As described for Table 1, the right hand column of Table 2 contains one cell for every possible permutation and combination of sensor and sensor data range/state. Some or all of these cells can be linked to outputs such as predictions, alerts or control signals. For example, the cell reached through the path of BSI Influent—Red; BSI Reactor—Red; and ABR—Red can be linked to an Alert sent to the system operator indicating that there is severe toxicity in the influent and bioreactor and a very low quantity of active biomass in the bioreactor. This Alert may be linked to a recommendation to mitigate sources of toxicity and then consider reseeding the bioreactor.

In another example, the industry is wastewater treatment and the application is activated sludge and microbial population data for a set of microorganisms is used. The parameters are cATP (which may red, yellow or green), filamentous bacteria (FB) concentration (which may be above or below a threshold) and dissolved oxygen (DO) concentration (which may be high or low). As an example of an analytical result, the cell reached through the path of c-ATP—Red; FB—Above Threshold; DO—Low can be linked to an Alert sent to the system operator indicating that sludge bulking is likely occurring in the bioreactor. This Alert may be linked to a recommendation to a) consider chlorinating the return activated sludge or b) increase aeration in the bioreactor.

Table 3 gives an example of a decision tree for a municipal water distribution network. Metals are monitored because they indicate corrosion, which may be microbially induced corrosion. As an example of analytical results, the cell reached through the path of c-ATP—Red; Biocide—Low; Metals—Positive can be linked to an Alert sent to the system operator indicating that microbially induced corrosion is likely occurring due to low biocide concentrations. This Alert may be linked to a recommendation to increase biocide dosage.

TABLE 3

| cATP | Biocide | Metals |
|---|---|---|
| Red | Low | Positive |
|  |  | Negative |
|  | Medium | Positive |
|  |  | Negative |
|  | High | Positive |
|  |  | Negative |
| Yellow | Low | Positive |
|  |  | Negative |
|  | Medium | Positive |
|  |  | Negative |
|  | High | Positive |
|  |  | Negative |
| Green | Low | Positive |

TABLE 3-continued

| cATP | Biocide | Metals |
|---|---|---|
| | | Negative |
| Medium | Positive | |
| | | Negative |
| High | Positive | |
| | | Negative |

In another example, the industry is oil and gas and the application is frac water treatment. The parameters are cATP (which may red, yellow or green), hydrogen sulfide concentration (which may be high or low) and concentration of hydrogen sulfide producing bacteria (which may be above or below a threshold). As an example of an analytical result, the cell reached through the path of c-ATP—Red; Hydrogen Sulfide—High; Hydrogen Sulfide Producing Bacteria—Above Threshold can be linked to an Alert sent to the system operator indicating that hydrogen sulfide producing bacteria population is uncontrolled. This Alert may be linked to a recommendation to increase biocide dosage using a biocide that does not react with hydrogen sulfide.

In another example, the industry is drinking water and the application is chlorinated municipal water supply. The parameters are cATP (which may red, yellow or green), total chlorine concentration (which may be high or low) and concentration of nitrifying bacteria (which may be above or below a threshold). As an example of an analytical result, the cell reached through the path of c-ATP—Red; Chlorine—Low; Nitrifying Bacteria—Above Threshold can be linked to an Alert sent to the system operator indicating that the nitrifying bacteria population is uncontrolled. This Alert may be linked to a recommendation to a) flush the system to reduce water age and increase chlorine residual or b) increase the chlorine-ammonia ratio.

In some examples, the thresholds between the ranges and the predictions/alert are at least initially selected based on expert opinion. In other examples, the thresholds between the ranges can be initially selected arbitrarily, by a user, by statistical analysis of data from the selected system or multiple systems (i.e. X standard deviations from ideal or from the average of data in a set or from a historical average) or by machine learning applied to a set of training data from the selected system or multiple systems.

Optionally, either the thresholds between ranges or the results associated with a cell may be modified over time based on experience with the selected system or, preferably, multiple similar water systems in the decision support system. Instances of predictions or alerts being made and followed or not followed by system operators are recorded. Instances were a prediction/alert is responded to and operation of the water system improves are considered positive results. Instances where a prediction or alert is ignored by the system operator and the operation of the water system deteriorates are also considered positive results. Conversely, instances where a prediction or alert is responded to and the operation of the water system does not improve or deteriorates are considered negative results. Instances where a prediction or alert is not responded to and the operation of the water system does not deteriorate or improves are also considered negative results. The decision support system uses machine learning to adjust the thresholds to provide more positive results and/or less negative results. For example, the decision support system periodically tests one or more thresholds to determine whether past results would have shown an improvement if the threshold had been higher or lower. When a change in a threshold is materially correlated with improved results, the threshold is changed. Other rules may also be applied. For example, any prediction/alert initially entered in the system that does not produce material net positive results or that produces an unacceptable frequency of negative results (optionally no negative results) is suspended until such time, if ever, changes in the thresholds applied retroactively to the data indicate that material net positive results or an acceptable frequency of negative results would be obtained under the new thresholds. Changes in thresholds and the suspension or activation of predictions/alerts may be allowed to occur automatically in the system or require human approval.

Optionally, the DSS 10 may bias (weigh) data from the most similar water systems to the selected water system and de-weigh, convert or translate data from water systems further away from the selected water system of interest. Alternatively, data from all water systems within a range may be converted to a common model process flow diagram, the DSS 10 operated on the common model process flow diagram, and results then converted back from the common model to the selected water system of interest.

Once the DSS 10 is operating on data from at least one water system 16, Case-Based Reasoning (CBR) can be used to set the initial thresholds between states and outputs for a new water system. The DSS 10 first retrieves one or more water systems in the database that are similar to the new water system. The DDS 10 then decides to reuse (if sufficiently similar) or adapt (if required) a retrieved water system to complete the thresholds and outputs for the new water system. The proposed solution is then evaluated via a simulated model or human agent and, if deemed likely to be successful, added to the DSS 10.

The DSS may also adjust thresholds over time by favoring any results that give preferred performance, for example wherein a water system is stable and a material measure of performance is at a high level, i.e. materially better than average. For example, the center or bounds of a "green" or other state associated with desirable operation may move to capture data correlated with high performance.

The decision support system may also have various other optional functions, which may be used alone or as part of machine learning. For example, the decision support system may have alerts triggered by any parameter entering a "red" range, departing from a historical (optionally temporally, i.e. seasonally, adjusted) range for the selected water system, going outside a range representing normal operation (i.e. operation within one standard deviation from average) for all water systems in the decision support system, or going outside of any user or otherwise specified range. For example, an increase in BSI in a reactor in an activated sludge plant above historical averages may cause an alert suggesting a check for incoming toxicity using a toxicity workflow protocol.

In another optional function, the decision support system may use a correlation analysis to identify correlations, or the lack of expected correlations, in data sets. In some examples, the correlations are between microbial population data such as ATP and other data. In these examples, the correlations allow identification of biomass growth limiting parameters and growth enabling parameters. For example, an observation that influent BOD is not correlating with ATP in the bioreactor of an activated sludge system can trigger an alert that the system is not optimized (i.e. ATP is being limited by other factors). The correlation analysis may incorporate a time differential between parameters to account for expected delays between normally correlated inputs and effects. For example, a slightly toxic compound entering a bioreactor may cause ATP to decrease hours to days later, and an increase in effluent BOD later still. The correlation analysis may apply pre-selected time delays or test various time delays to determine the time delay that produces the strongest correlation. Expected correlations can be checked against other water systems in the decision support system.

Various hardware systems may be used in the system. For example, the analysis may be performed on a MICROSOFT R Server with data analysis functions written locally (in server interface computer 14) in R and run on cloud-based servers for real time analysis.

In the examples above, the output of the decision support system is an alert or prediction sent to a water system operator. The system operator then adjusts operation of the water system 16. Alternatively, the decision support system may be used to directly control some or all functions of a water system 16.

In the description above, decision tree programming is used. However, the system may use other forms of programming such a fuzzy logic. A fuzzy logic based system can be programmed to produce one or more alerts or predictions as described above, or alternatively numerical outcomes usable as a control signal. The fuzzy logic system preferably has at least two input sensors 22, for example at least one ATP based sensor and at least one other sensor incorporating non-ATP data. In a fuzzy logic implementation, data from the sensors 22 is categorized into multiple states or classes. The degree of membership of the variable in each class is determined using a membership function that maps the variable to a truth value in a predefined range, for example between 0 and 1. The decision support system 10 then applies a plurality of rules that consider the degrees of membership of each variable in its corresponding classes. The decision support method further includes considering the result of a plurality of the rules to determine an output. The output can relate to an issue such as—is there evidence of unintended toxicity in the system? or, is sludge age near an optimum? Several outputs can be provided simultaneously. The output is typically a number, but the output number can then be mapped through an output function to one or more of a set of alerts or recommendations. Alternatively, the output can be used as a control signal, directly or through an output function. Changing either the shape of the membership functions, the rule set including the combination function, or the output function, modifies the decision support output. Similar to the decision tree based methods described above, machine learning can be used to change any of the fuzzy logic functions based on data from the selected plant or other plants.

In an example, the DSS 10 considers bioreactor ATP and another parameter. In each iteration of its program, the DSS 10 receives input values corresponding to the ATP and other parameter. The input values may be an average over a preceding period of time. The input values are converted by dividing over their maximum possible values into a number between 0 and 1. Each value is then applied to its corresponding class membership function. Membership in a class is considered "true" only if the resulting value is not 0. For example, a certain ATP value may be 0 (false) for red, 0.6 true for green and 0.4 true for yellow. The other parameter may be, for example, 0.2 true for high and 0.8 true for low. To this point, the fuzzy logic implementation is like the decision tree but the sharp lines between classes at nodes in the decision tree have been fuzzified by membership functions other than step functions.

Next, rules (calculations) that involve an ATP input value that is true for yellow or green and a second parameter that is true for high or low are selected from a set of all rules and evaluated to give output variables. Next, the results of evaluations under these rules (the output variables) are combined according to a combination function. The combination function produces an output, for example a weighted average of the output variables. Optionally, the output can be converted again through an output function into a different number or into discrete alerts or predictions like those associated with some of the right hand column cells in the decision tree method. For example, one set of rules, combination function and output function can be used to predict that toxicity is likely present, might be present, or is not present another example. In another example, a set of rules, combination function and output function can be used to predict that sludge age is too high, near optimum, or loo low.

The fuzzy control algorithm can be tuned by adjusting the membership functions, the rules applied to the input values to give the output variables, or the weighting (or other combination function attributes) given to the output variables to produce the combined output. The tuning can be done considering data from other water systems in the decision support system as described above for the decision tree process.

We claim:

1. A decision support system for a water system comprising,
   an interface program operable on a user interface device at a water system;
   an analytical program operable on a remote server; and,
   one or more data collection devices at the water system including at least one device that provides microbial population data,
   wherein,
   the analytical program is configured to (a) compare data collected from the water system against numerical values and to modify one or more of the numerical values considering historical data from similar water systems, or (b) compare data collected from the water system against a rules based decision system, wherein the rules based decision system includes comparing data collected from the water system against numerical values, wherein one or more of the numerical values are modified considering historical data from multiple similar water systems.

2. The decision support system of claim 1 wherein the one or more data collection devices further comprises one or more devices for collecting data relating to one or more physical, chemical or electrical parameters of water.

3. The decision support system of claim 1 wherein the microbial population data includes AxP data.

4. The decision support system of claim 1 wherein the microbial population data includes microbial speciation data or metagenomic data.

5. The decision support system of claim 1 wherein the output includes an assessment of the current operation of the water system.

6. The decision support system of claim 1 wherein the output includes a prediction, recommendation or warning about the future operation of the water system.

7. The decision support system of claim 1 wherein the analytical program controls one or more aspects of the water system.

8. The decision support system of claim 1 wherein the water system, and any similar systems considered by the decision support system, are one of (i) an activated sludge plant, (ii) a municipal water distribution network, (iii) frac water treatment system and (iv) a drinking water treatment system.

9. The decision support system of claim 1 wherein the interface program includes a selection of water system models.

10. The decision support system of claim 1 wherein the analytical program is configured to compare the microbial population data to a threshold or to categorize the microbial population data into one or more ranges, states or classes.

11. A decision support method for a water system comprising the steps of,
   a) building a model of a water system;
   b) collecting data from the water system;
   c) comparing data from the water system (i) against numerical values that have been adjusted considering historical data from multiple similar water systems, or (ii) against a rules based decision system that includes numerical values that have been adjusted considering historical data from multiple similar water systems; and,
   d) producing an output considering the comparison,
   wherein the data includes microbial population data.

12. The method of claim 11 wherein the data further comprises one or more physical, chemical or electrical parameters of water in the water system.

13. The method of claim 11 wherein the microbial population data includes AxP data.

14. The method of claim 11 wherein the microbial population data includes microbial speciation data or metagenomic data.

15. The method of claim 11 wherein the output includes an assessment of the current operation of the water system.

16. The method of claim 11 wherein the output includes a prediction, recommendation or warning about the future operation of the water system.

17. The method of claim 11 wherein the output includes controlling one or more aspects of the water system.

18. The method of claim 11 wherein the water system, and any similar systems involved in the method, are one of (i) an activated sludge plant, (ii) a municipal water distribution network, (iii) frac water treatment system and (iv) a drinking water treatment system.

19. The method of claim 11 comprising selecting the model from a set of pre-determined models.

20. The method of claim 11 comprising comparing the microbial population data to a threshold or categorizing the microbial population data into one or more ranges, states or classes.

* * * * *